United States Patent [19]
Scholz

[11] Patent Number: 4,935,018
[45] Date of Patent: Jun. 19, 1990

[54] HOOF DRESSING APPLICATOR

[76] Inventor: Sharon R. Scholz, 3020 Symphony La., Huntingtown, Md. 20639

[21] Appl. No.: 386,006

[22] Filed: Jul. 25, 1989

Related U.S. Application Data

[63] Continuation of Ser. No. 184,508, Apr. 21, 1988, abandoned.

[51] Int. Cl.[5] .............................................. A61F 13/00
[52] U.S. Cl. .................................... 604/306; 606/212; 604/289; 128/165
[58] Field of Search ............... 128/155, 157, 165, 336; 604/289, 306, 307, 304; 424/443, 445, 446, 447, 449; 401/132, 133; 54/82; 168/2; 606/212

[56] References Cited

U.S. PATENT DOCUMENTS

| | | | |
|---|---|---|---|
| 3,116,732 | 1/1964 | Cahill | 604/306 |
| 3,118,449 | 1/1964 | Bane | 128/336 |
| 3,366,112 | 1/1968 | Antonik | 128/157 |
| 3,682,179 | 8/1972 | Firth et al. | 128/336 |
| 4,140,116 | 2/1979 | Hampicke | 54/82 |
| 4,548,026 | 10/1985 | Shidner | 168/2 |
| 4,666,441 | 5/1987 | Andriola et al. | 604/304 |

OTHER PUBLICATIONS

The American Heritage Dictionary, 2nd Ed., Houghton Mifflin Co. (1982), pp. 621, 496.

*Primary Examiner*—Richard J. Apley
*Assistant Examiner*—Paul Prebilic
*Attorney, Agent, or Firm*—H. Jay Speigel

[57] ABSTRACT

A hoof dressing applicator having an applicator band for direct attachment to the coronary band of a horse's hoof. The applicator band has three rows with each row having three sealed pouches containing equal amounts of medication totalling a two-days' supply. Each pouch has a thick tough plastic exterior wall portion superposed over a weak thin plastic interior wall portion rupturable by sufficient pressure applied to its corresponding exterior wall portion. The double-seamed margings of the pouches in common with one another are joined together by heat-sealing. A thick, flexible, soft felt backing is carried by the interior wall portions of the pouches and interfaces with the coronary band of the horse's hoof. Sufficient pressure against the exterior wall portions along a row ruptures its three interior wall portions of such pouches with slow flowing of the medication which is soaked-up the felt backing and continously applied to the coronary band. Thereafter, the horse itself therapeutically medicates itself with medication by the horse's own natural movements of its legs to thereby continually massage the medication into its coronary band.

19 Claims, 4 Drawing Sheets

FIG. 1
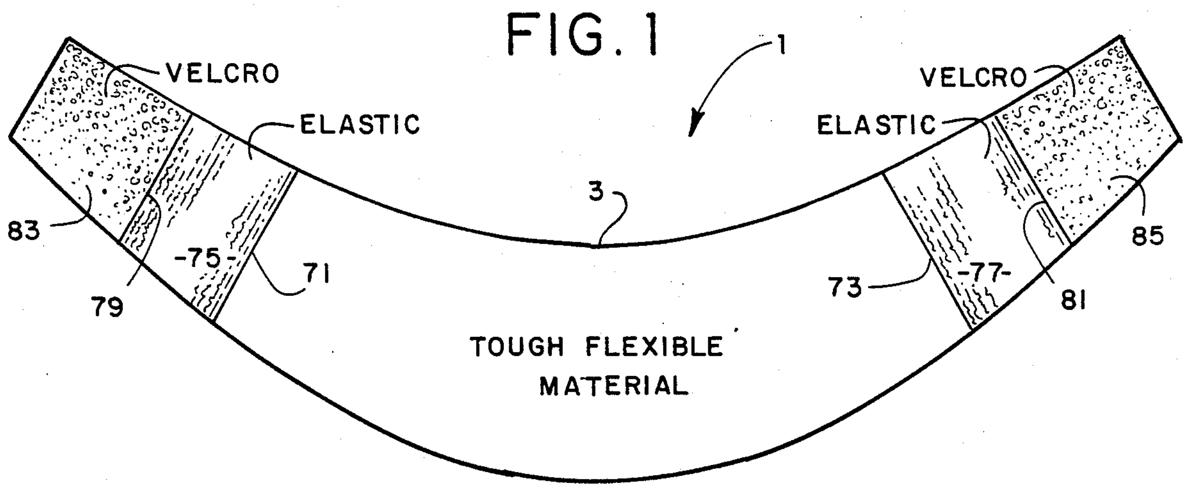
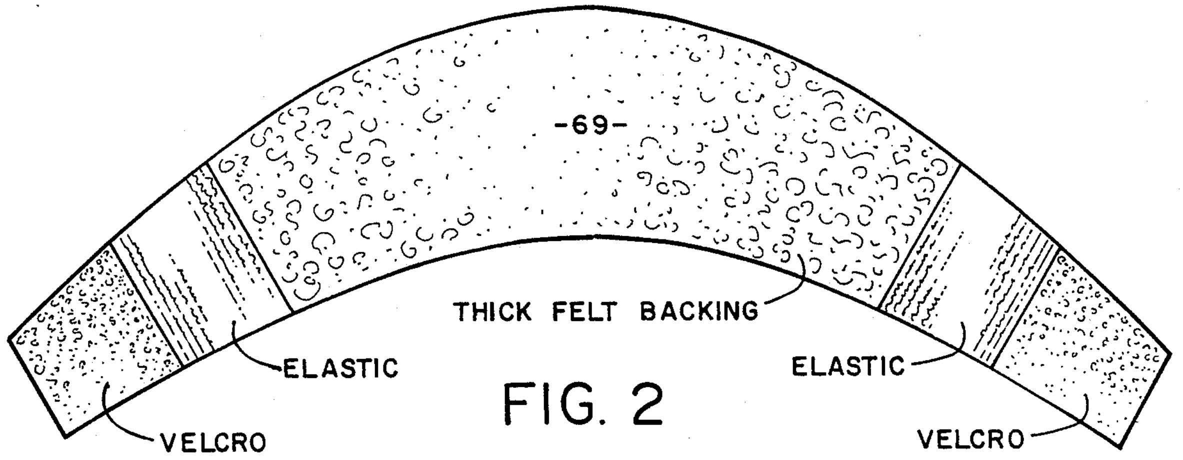
FIG. 2
FIG. 3
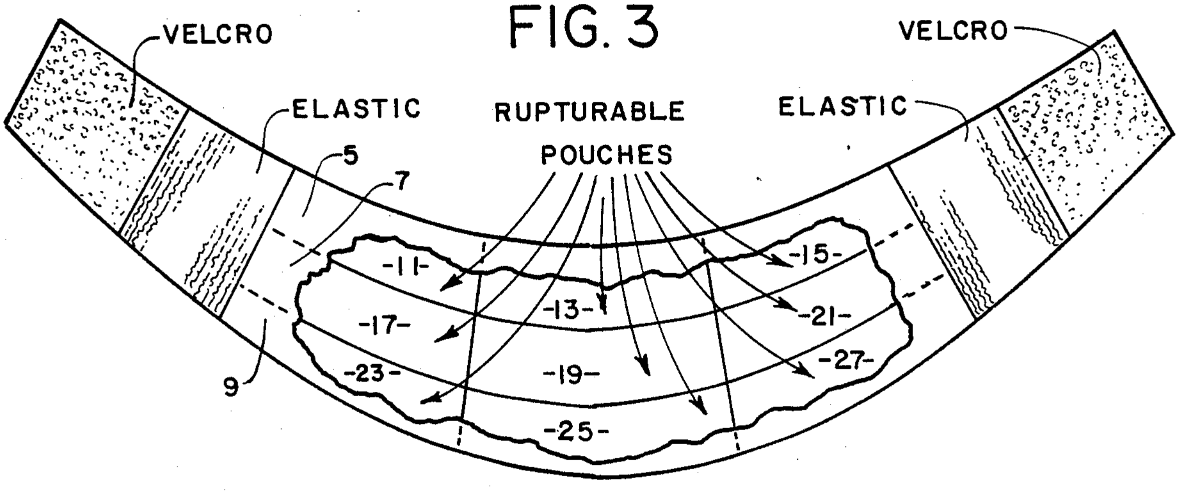

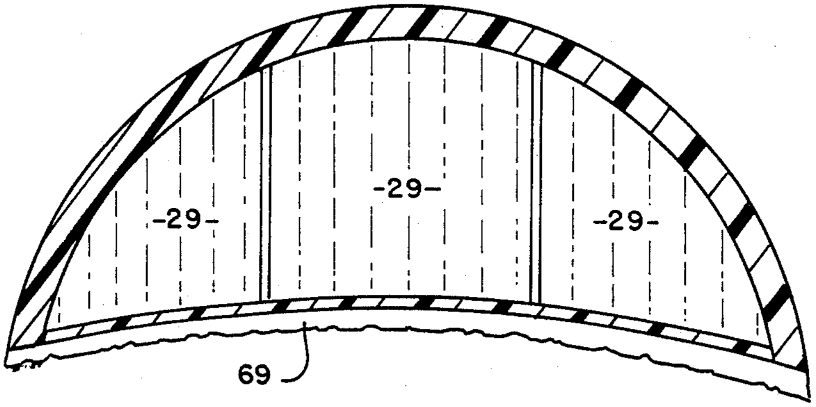
FIG. 4
FIG. 5
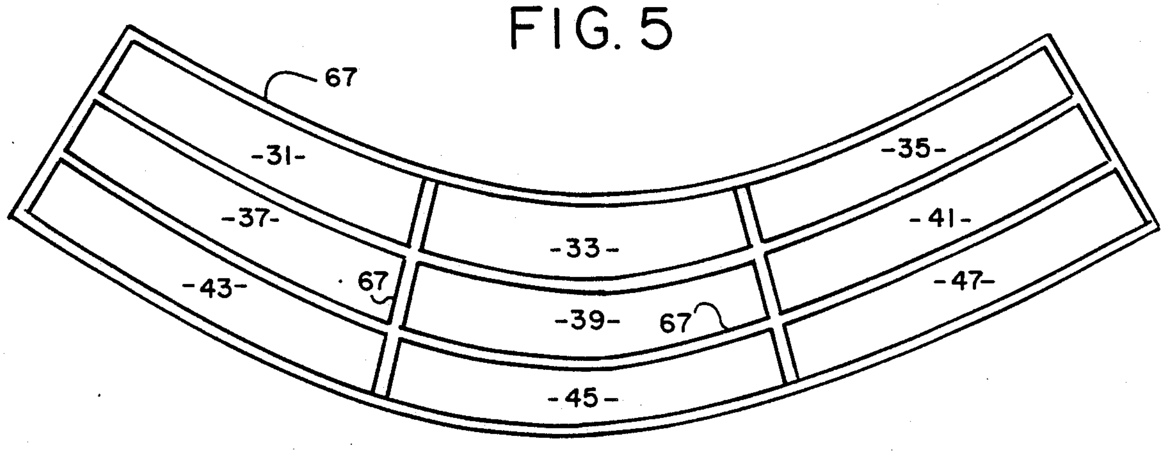
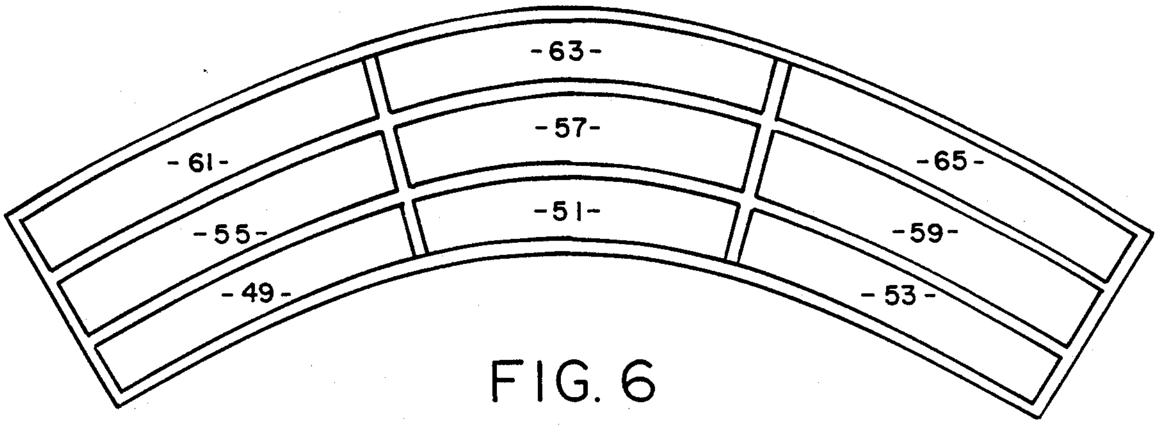
FIG. 6

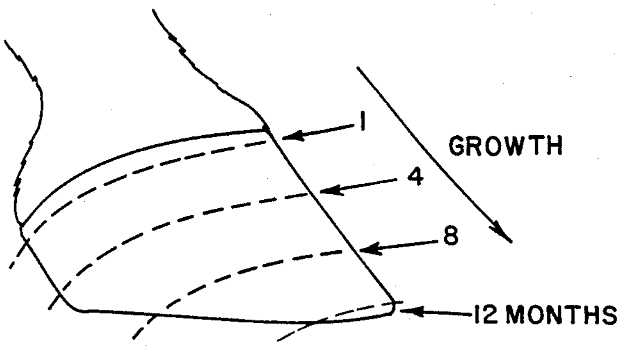
FIG. 7a
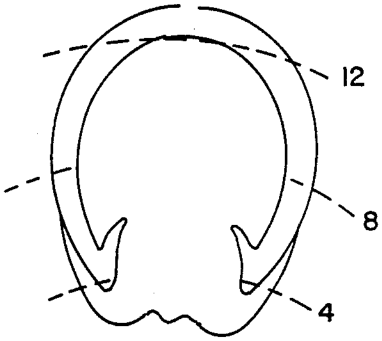
FIG. 7b
FIG. 8a
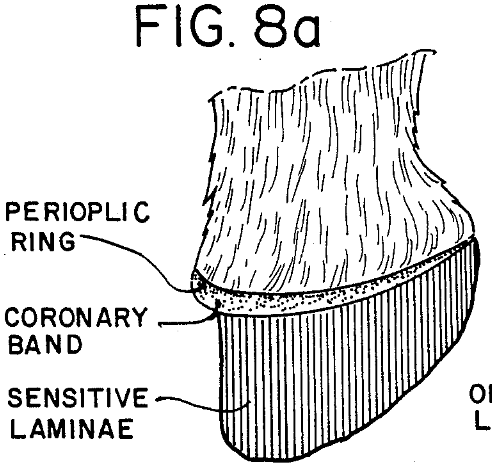
FIG. 9a
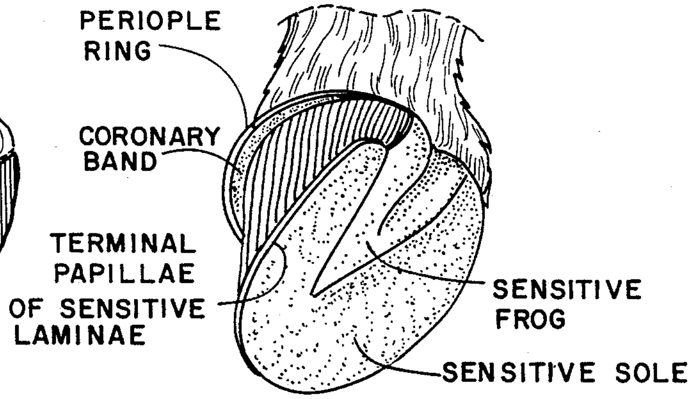
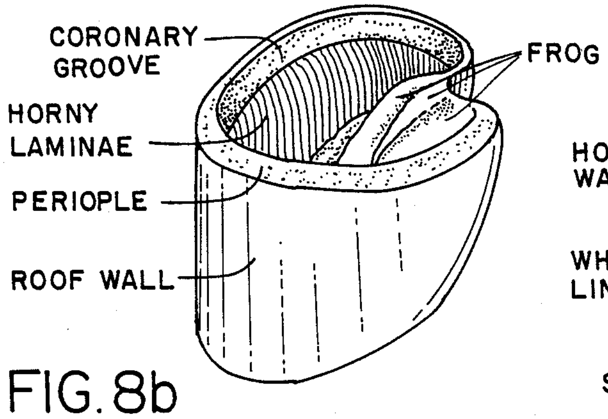
FIG. 8b
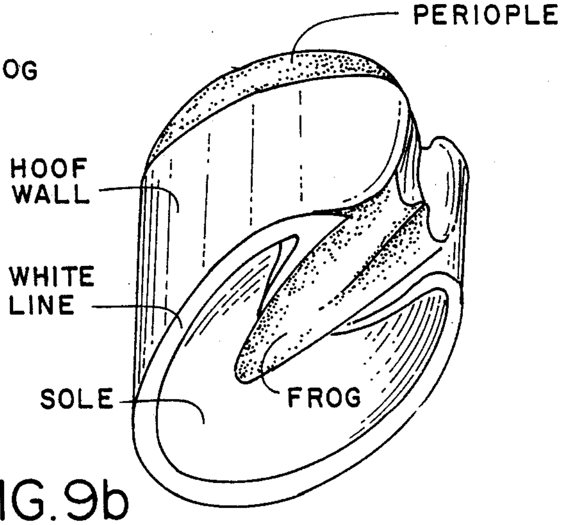
FIG. 9b

HOOF DRESSING APPLICATOR

This application is a continuation of application Ser. No. 184,508 filed Apr. 21, 1988.

BACKGROUND OF THE INVENTION

1. Technical Field

This invention relates to a hoof dressing applicator that is attached to each one of the coronary bands of a horse's hooves to apply hoof dressing to such coronary band and to massage such hoof dressing medication into such coronary band to maintain the proper percentage of moisture into the horse's hooves and maintain sound hoof structure and growth, and to prevent thereby cracking of the horse's hooves.

2. Background

A horse's sensitive coronary band is located around the upper per border of the hoof under its junction with the skin. The coronary band is the primary growth and nutritional source for the balk of the hoof wall. The horn producing papillae of the coronary band produce the hoof wall. The function of the hoof wall is to bear weight. The hoof wall grows downwardly at the rate of about ¼" to ⅜" per month. The average horse's hoof is 3 to 4 inches. Therefore, it can be said that the horse grows new hooves every year. The hollow centers of the horn tubules are filled with random, loosely packed cells forming a pitch-like substance called the intratubular horn. The intratubular horn is largely responsible for moisture conduction. For the hoof wall to be healthy, and to promote and maintain sound hoof structure and growth, and to prevent cracking of the horse's hoof, the moisture content of the hoof wall must be maintained at about 25%.

The practice in the prior art to maintain such proper moisture level is to apply hoof dressing medication to the coronary band of each hoof several times a day. The horse's owner or handler accomplishes this by applying the hoof dressing medication to the coronary band with a toothbrush and by massaging the medication into the coronary band. This prior-art practice is not only burdensome and time-consuming, but also is frequently left undone or done incompletely. Another problem is that the horse's owner or handler, in performing such prior-art practice, risks being kicked by the horse.

The problems in the art are the needs for a hoof dressing applicator which can be attached to the coronary band of a horse's hoof to release and therefore apply moisture to the coronary band with consequent self-massaging of the medication into the coronary band being continually effected by the horse's own natural movements of its legs whether the horse is in its stall or ranging in the field. In other words, the need is for a hoof dressing applicator that can be attached to the coronary band with the horse itself taking over and in effect therapeutically medicating and massaging its own coronary bands, continually.

SUMMARY OF THE INVENTION

The objects of the invention are to contribute to the solution of the discussed problems of the prior art by providing a hoof dressing applicator having an applicator band that can be attached directly to each of the coronary bands of the horse's hooves. The applicator band has three elongated rows, i.e., a top row, middle row and bottom row. Each row is subdivided into and has three sealed pouches containing equal amounts of hoof dressing medication. Each row has a left lateral pouch, a central pouch and a right lateral pouch. The three pouches of each row together contain sufficient hoof dressing medication for a two-days' application period. Each pouch has a tough exterior wall portion of suitable plastic material and a superposed weak interior wall portion of thin plastic material that can be ruptured by manual hand-pressure applied against its corresponding tough exterior wall portion. The double-seamed margins of the pouches in common with one another are joined together by appropriate heat-sealing. The interior wall portions of the puches are disposed in interfacing-relationship with the coronary band of the horse's hoof. A thick, soft, flexible felt backing is appropriately fixed to the interior wall portions of the left lateral, central and right lateral pouches of all three rows, and is interposed between the three rows and the coronary band. The lateral ends of the left lateral and right lateral pouches are suitably fixed to intermediate portions of suitable elastic material, and the ends of such intermediate portions are joined to terminal hook and pile fasteners such as those marketed using the Trademark VELCRO. The applicator band is appropriately disposed and wrapped tightly and securely around the coronary band with the terminal hook and pile fastener portions engaged. All the horse's owner or handler needs to do thereafter is to apply sufficient hand pressure along and against one of the rows to rupture the left lateral, central and right lateral pouches of that particular row to start the medication flowing slowly to be soaked up by the thick felt backing. The medication soaked up by the felt backing will thereby be slowly applied to the coronary band. Thereafter, the horse takes over. The horse, by its own natural movement of its legs, will therapeutically medicate itself with medication and massage the hoof dressing medication into its own coronary bands. After the elapse of two days, another row of pouches is similary ruptured by human intervention. After the third and last row of pouches are ruptured and subsequent two days have elapsed, the applicator band is removed and replaced by a new applicator band.

BRIEF DESCRIPTION OF THE DRAWINGS

These objects and other objects of the invention should be discerned and appreciated by the description of the preferred embodiment taken in conjunction with the drawings, wherein like reference numeral refer to similar parts throughout the several views, in which:

FIG. 1 is a front exterior view of the applicator band;

FIG. 2 is a rear view of the applicator band shown in FIG. 1;

FIG. 3 depicts the applicator band, shown in FIG. 1, partly broken-away to show the three rows of rupturable pouches;

FIG. 4 represents a cross-sectional view of the applicator band shown in FIG. 1 and shows the three rows of pouches filled with horse dressing medication;

FIG. 5 shows the front exterior view of the plastic pouches whose double-seamed margins in common with one another are joined together by heat-sealing;

FIG. 6 shows the rear interior view of the plastic pouches;

FIG. 7*a* is a side elevational view showing the rate of growth and age of the hoof wall;

FIG. 7*b* is a bottom view of the rate of growth shown in FIG. 7*a;*

FIG. 8*a* shows the position and relationship of the sensitive structures with respect to the hoof structures shown in FIG. 8*b;*

FIG. 8*b* shows the hoof structures with respect to the sensitive structures shown in FIG. 8*a;*

FIG. 9*a* is a rearward aspect showing the position and relationship of the sensitive structures with respect to the same aspect of the hoof structures shown in FIG. 9*b;*

FIG. 9*b* shows the same aspect of the hoof structures with respect to the aspect of the sensitive structures shown in FIG. 9*a;*

DESCRIPTION OF THE PREFERRED EMBODIMENT

Figure 10:
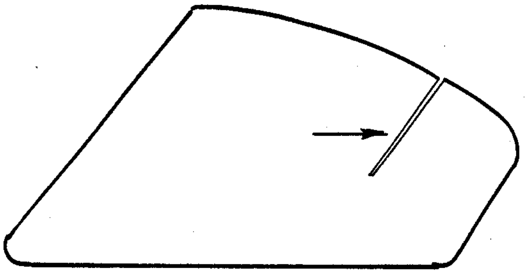
FIG. 10 shows a hoof-quarter-sandcrack type of injury that the applicator band of this invention prevents or, if theretofore sustained, thereafter therapeutically repairs and heals.

In FIG. 1 of the drawings, reference numeral 1 generally refers to the hoof dressing applicator of this invention. For examples, the hoof dressing medication utilized may be that which is marketed using one of the following Trademarks: (a) VITAHOOF by Ann Lang Greshan, manufactured by Racehorse Veterinary Products, 5809 Warren Farm, Route 2, Hiram, Ga. 30141; (b) MOLLIMENTUM HOOF DRESSING, made by Troy Chemical Division, Y-Tex Corp., Cody, Wyo. 82414; (c) ABSORBINE HOOFLEX, made by W. F. Young, Inc., Springfield, Mass. 01103; (d) RAINMAKER made by Farna Companies Incorporated, Omaha, Nebr. 68112; or other similar suitable types of medication.

Applicator 1 has an enlarged applicator band 3 that is arcuately configures to conformably fit and complementally engage the exterior region generated by the coronary band of the horse's hoof, as shown in FIGS. 8*a* and 8*b*. Applicator band 3 has three elongated rows with three pouches in each row, to wit: a top row 5, a middle row 7 and a bottom row 9. The top row 5 has a left lateral pouch 11, central pouch 13 and right lateral pouch 15. The middle row has a left lateral pouch 17, a central pouch 19 and a right lateral pouch 21. The bottom row 9 has a left lateral pouch 23, a central pouch 25 and a right lateral pouch 27. The pouches contain equal quantities of the hoof dressing medication 29. Pouches 11, 13, 15, 17, 19, 21, 23, 25 and 27 have tough exterior plastic wall portions 31, 33, 35, 37, 39, 41, 43, 45 and 47, respectively; and rupturable thin plastic interior wall portions 49, 51, 53, 55, 57, 59, 61, 63 and 65, respectively. The double-seamed margins 67 of the pouches are joined to one another by appropriate heat-sealing. A thick, soft, flexible felt backing 69, corresponding to the area generated by the pouches, is suitably fixed to the thin wall plastic wall portions of the pouches. The left and right lateral margins 71 and 73 are suitably fixed to respective left and right intermediate portions 75 and 77 of suitable elastic material. The left and right lateral ends 79 and 81 of the respective left and right intermediate portions 75 and 77 are suitably fixed to respective left and right terminal Velcro portions 83 and 85.

OPERATIONAL DESCRIPTION

Figure 11:
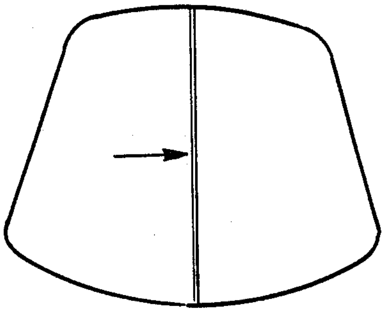
FIG. 11 shows a complete-toe-sandcrack type of injury that the applicator band of this invention prevents or, if theretofore sustained, thereafter therapeutically repairs and heals.
Figure 12:
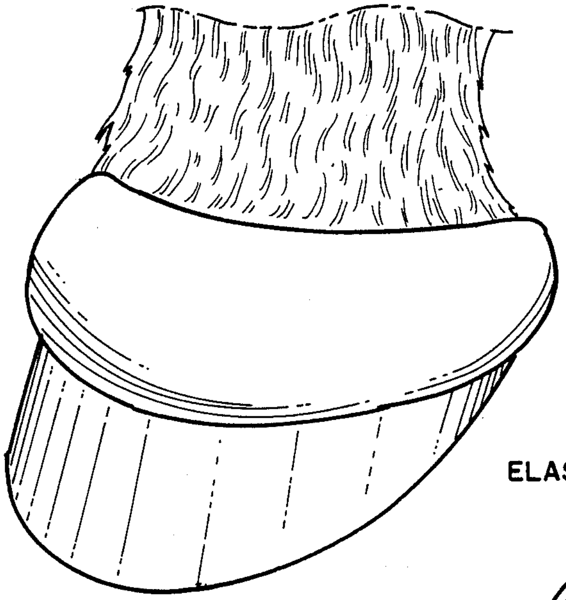
FIG. 12 is a front view showing the applicator band attached to a horse's hoof relative to its coronary band.
Figure 13:
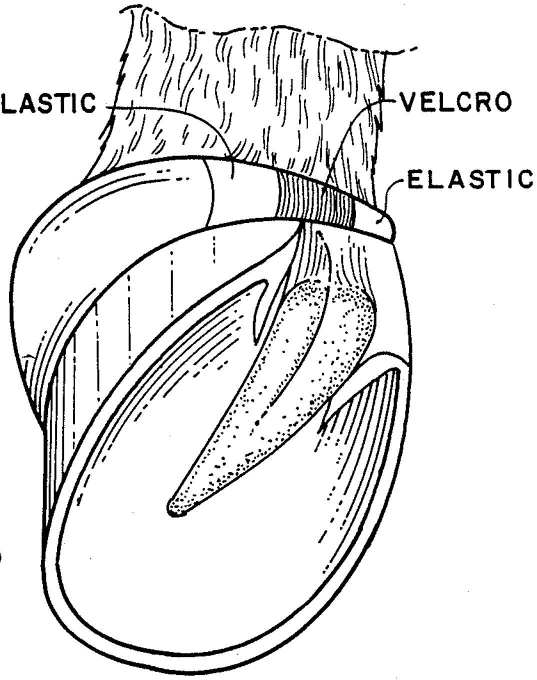
FIG. 13 is a rearward aspect showing the applicator band attached relative to the coronary band of a horse's hoof.

In operational use, the applicator band 3 is appropriately disposed and wrapped around the coronary band of the horse's hoof with the thick felt backing 69 disposed against the coronary band. The intermediate elastic portions 75 and 77 are appropriately stretched with the hook and pile portions 83 and 85 being thereafter engaged to achieve and effect tight engagement of the applicator band 3 with the coronary band of the horse's hoof. In the event the horse is free-ranging in the field, no problem will be presented of the horse being injured or otherwise immobilized in one of the applicator bands 3 is snagged or caught upon an object, for the reason that the hook and pile portions 83 and 85 of such snagged applicator band 3 will disengage with the applicator band 3 falling away. To start the hoof dressing medication 29 slowly flowing and being soaked up by the felt backing 69, manual pressure is simply applied along one of the rows 5, 7 or 9. For example, the horse's owner or handler would apply sufficient manual pressure in turn against the exterior wall portions 37, 39 and 41 of the middle row 7 to effect rupture of the respective thin wall portions 55, 55 and 59. This would start the medication 29 slowly flowing from the respective pouches 17, 19 and 21 and being soaked up by the felt backing 69, and being applied to the coronary band to maintain proper moisture content in the horse's hoof, to promote and maintain sound hoof structure and growth, and to thereby prevent cracking of the horse's hoof. If the horse already has the types of hoof injuries shown in FIGS. 10 and 11, the applicator band 3 by application thereto of the medication 29 will repair and heal same. The natural movements of the horse's legs, whether the horse is in its stall or in the field, will cause the thick felt backing 69, soaked-up with medication 29, to be applied therapeutically to the coronary band continually along with being massaged into the coronary band. Thus it can be said that once a row is ruptured by human intervention, the horse itself takes over to therapeutically to self-administer the hoof dressing medication 29 by the horse's own natural movements of its legs. Since a row of pouches containing the medication 29 lasts two days, human intervention is only necessary to rupture another row of pouches with the horse itself again taking care of its own therapeutic administratiuon of the hoof dressing medication 29. After six days, the old applicator bands 3 are removed from the coronary bands of the horse's hooves and new applicator bands 3 are attached.

I claim:

1. A hoof dressing applicator band means for attachment to the coronary band of a horse's hoof to continuously apply hoof dressing medication to said coronary band comprising sealed pouch means and attachment means; said sealed pouch means containing said hoof dressing medication, said attachment means being provided for wrapping said applicator band means around the coronary band of the horse's hoof and securing said applicator band means thereto, said sealed pouch means being rupturable to slowly release and continuously apply said medication to said coronary band, whereby sound hoof structure and growth are promoted and maintained and cracking of said hoof is substantially prevented, said applicator band means being elongated so that when said applicator band means is secured on said hoof, said applicator band means substantially solely covers said coronary band of said hoof, said sealed pouch means comprising at least one elongate row of sealed pouches having a plurality of sealed pouches in each said at least one row thereof and said at least one row being substantially aligned along a longitudinal axis of said applicator band means, each said sealed pouch being individually rupturable.

2. The invention of claim 1, wherein said pouch means has a tough exterior wall portion means of suitable material and superposed weak interior wall portion means of suitable material rupturable by pressure application against said exterior wall portion means to slowly release said hoof dressing medication, and said interior wall portion means being disposed in interfacing relationship with said coronary band.

3. The invention of claim 1, said applicator band means having medication retaining means, said medication retaining means being interposed between said pouch means and said coronary band when said applicator band means is wrapped thereabout and said medication retaining means soaking up medication released from said rupturable pouch means and applying said medication to said coronary band.

4. The invention of claim 1, wherein said attachment means has terminal hook and pile fastening means.

5. The invention of claim 1, wherein said attachment means has elastic means.

6. The invention of claim 1, wherein said attachment means has intermediate elastic means and terminal hook and pile fastening means.

7. The invention of claim 1, wherein said pouch means comprises a plurality of elongated rows of pouches and wherein each said pouch contains sufficient medication for a fixed period of time.

8. The invention of claim 7, wherein each row has a left lateral, a central and a right lateral pouch.

9. The invention of claim 8, wherein adjacent said pouches have common margins and wherein said adjacent said pouches are joined together with one another at their said common margins.

10. The invention of claim 1, wherein said applicator band means has medication retaining means and wherein said medication retaining means comprises a thick backing of suitable medication retaining material.

11. The invention of clam 10, wherein said suitable medication retaining material comprises soft felt material.

12. The invention of claim 1, wherein said pouch means is made of suitable plastic material.

13. The invention of claim 2, wherein said suitable material of said exterior wall portion means comprises thick plastic material and wherein said suitable material of said interior wall portion means comprises thin plastic material.

14. The invention of claim 1, wherein said pouch means comprises a plurality of elongated rows of pouches, each said pouch containing sufficient medication for a fixed period of time, wherein each said row has a left lateral, a central and a right lateral pouch, wherein some of said pouches have common margins, wherein said some of said pouches are joined together with one another at their said common margins, wherein said pouches have tough exterior wall portion means of suitable thick plastic material and superposed weak interior wall portion means of suitable thin plastic material, wherein said weak interior wall portion means of said pouches is rupturable by suitable pressure application directed against said exterior wall portion means, and wherein said interior wall portion means are disposed in interfacing relationship with said coronary band when said band means is attached on the horse's hoof.

15. The invention of claim 14, wherein said applicator band means has medication retaining means, wherein said weak interior wall portion means carries said medication retaining means, wherein said medication retaining means is interposed between said interior wall portion means and said coronary band when said band means is attached on said horse's hoof, wherein said medication retaining means soaks up the medication slowly released from said pouches upon said weak interior wall portion means being ruptured and applies such released medication continuously to the coronary band, and wherein said medication retaining means comprises a thick, flexible backing of soft felt material.

16. An applicator for applying medication to a hoof of a horse comprising:

(a) container means for containing a supply of medication;

(b) attachment means connected to said container means for attaching said applicator around the coronary band of said hoof, said attachment means securing said applicator around said coronary band of said hoof;

(c) applying means for applying said medication released from said container on said hoof, said medication maintaining an amount of moisture in said hoof necessary to maintain sound hoof structure and to prevent hoof cracking;

(d) said applicator being elongated so that when said applicator is secured on said hoof, said applicator substantially solely covers said coronary band of said hoof;

(e) said container means comprising at least one elongate row of sealed pouches having a plurality of sealed pouches in each said at least one row thereof and said at least one row being substantially aligned along a longitudinal axis of said applicator band means, said applying means comprising each said sealed pouch being individually rupturable to slowly release and continuously apply said medication to said coronary band.

17. The invention of claim 16, wherein said container means includes a piece of material of sufficient thickness to allow retention of a supply of medication therein, said applying means further comprising a surface of said piece of material in engagement with said coronary band of said hoof when said applicator is attached thereon.

18. The invention of claim 16, wherein said attachment means comprises two elastic straps having hook and pile fastening means thereon.

19. The invention of claim 16, wherein said attachment means includes an elastic portion.

* * * * *